United States Patent
Li et al.

(10) Patent No.: US 8,285,371 B2
(45) Date of Patent: Oct. 9, 2012

(54) DYNAMIC SELECTION OF ALGORITHMS FOR ARRHYTHMIA DETECTION

(75) Inventors: Dan Li, Shoreview, MN (US); Jaeho Kim, Redmond, WA (US); Julie A. Thompson, Circle Pines, MN (US); Arjun Sharma, St. Paul, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 180 days.

(21) Appl. No.: 12/754,955

(22) Filed: Apr. 6, 2010

(65) Prior Publication Data
US 2010/0274146 A1 Oct. 28, 2010

Related U.S. Application Data

(60) Provisional application No. 61/171,723, filed on Apr. 22, 2009.

(51) Int. Cl.
*A61B 5/02* (2006.01)
(52) U.S. Cl. .......................... 600/515; 600/509; 600/518
(58) Field of Classification Search .............. 600/509, 600/515, 518
See application file for complete search history.

(56) References Cited

U.S. PATENT DOCUMENTS

| | | | |
|---|---|---|---|
| 4,773,401 A | 9/1988 | Citak et al. | |
| 5,002,052 A * | 3/1991 | Haluska | 607/4 |
| 5,311,874 A | 5/1994 | Baumann et al. | |
| 5,342,406 A | 8/1994 | Thompson | |
| 6,076,015 A | 6/2000 | Hartley et al. | |
| 6,666,826 B2 | 12/2003 | Salo et al. | |
| 6,873,870 B2 | 3/2005 | Ferek-Petric | |
| 6,889,081 B2 | 5/2005 | Hsu | |
| 7,010,344 B2 | 3/2006 | Burnes et al. | |
| 7,142,918 B2 | 11/2006 | Stahmann et al. | |
| 7,212,860 B2 | 5/2007 | Stahmann et al. | |
| 7,430,446 B2 | 9/2008 | Li | |
| 7,474,920 B2 | 1/2009 | Burnes et al. | |
| 7,582,061 B2 | 9/2009 | Li et al. | |

(Continued)

FOREIGN PATENT DOCUMENTS

| | | |
|---|---|---|
| EP | 0360412 A1 | 3/1990 |
| WO | WO-2007/024920 A2 | 3/2007 |
| WO | WO-2007/073455 A1 | 6/2007 |
| WO | WO-2008/024180 A1 | 2/2008 |

OTHER PUBLICATIONS

"International Application Serial No. PCT/US2010/030060, International Search Report mailed Jul. 19, 2010", 4 pgs.

(Continued)

*Primary Examiner* — Joseph Dietrich
(74) *Attorney, Agent, or Firm* — Schwegman Lundberg & Woessner, P.A.

(57) ABSTRACT

An apparatus comprises a first implantable sensor produces a first electrical sensor signal representative of cardiac depolarization events of a heart of a subject, a second implantable sensor that produces a second electrical sensor signal representative of hemodynamic function of the heart, a signal analyzer circuit, and an arrhythmia discrimination circuit. The signal analyzer circuit detects an arrhythmic event from the first sensor signal and calculates hemodynamic stability in response to the arrhythmic event detection using the second sensor signal. The arrhythmia discrimination circuit selects, according to a calculated hemodynamic stability produced by the signal analyzer circuit, an arrhythmia discrimination algorithm from among a plurality of candidate arrhythmia discrimination algorithms that are implementable by the arrhythmia discrimination circuit, classifies the detected arrhythmia using the selected arrhythmia discrimination algorithm, and provides the arrhythmia classification to a user or process.

18 Claims, 6 Drawing Sheets

U.S. PATENT DOCUMENTS

| | | |
|---|---|---|
| 2003/0125774 A1 | 7/2003 | Salo |
| 2003/0204209 A1 | 10/2003 | Burnes et al. |
| 2004/0127792 A1 | 7/2004 | Siejko et al. |
| 2004/0225332 A1 | 11/2004 | Gebhardt et al. |
| 2006/0217621 A1 | 9/2006 | Kim et al. |
| 2006/0281998 A1 | 12/2006 | Li |
| 2007/0043394 A1 | 2/2007 | Zhang et al. |
| 2007/0149890 A1 | 6/2007 | Li et al. |
| 2007/0203524 A1 | 8/2007 | Sheldon et al. |
| 2007/0239218 A1 | 10/2007 | Carlson et al. |
| 2007/0249945 A1 | 10/2007 | Li et al. |
| 2007/0260283 A1 | 11/2007 | Li |
| 2008/0045851 A1 | 2/2008 | Cazares et al. |
| 2008/0051843 A1 | 2/2008 | Li et al. |
| 2008/0281367 A1 | 11/2008 | Zhang et al. |
| 2009/0131999 A1 | 5/2009 | Li et al. |
| 2009/0254137 A1 | 10/2009 | Salo et al. |

OTHER PUBLICATIONS

"International Application Serial No. PCT/US2010/030060, Written Opinion mailed Jul. 19, 2010", 7 pgs.

Srinivasan, V., et al., "Spontaneous gasping decreases intracranial pressure and improves cerebral perfusion in a pig model of ventricular fibrillation.", *Resuscitation, 69(2)*, (May 2006), 329-34.

* cited by examiner

DYNAMIC SELECTION OF ALGORITHMS FOR ARRHYTHMIA DETECTION

CROSS REFERENCE TO RELATED APPLICATION

This application claims the benefit of U.S. Provisional Application No. 61/171,723, filed on Apr. 22, 2009, under 35 U.S.C. §119(e), which is hereby incorporated by reference.

BACKGROUND

Implantable medical devices (IMDs) are devices designed to be implanted into a patient. Some examples of these devices include cardiac function management (CFM) devices. CFM devices include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect abnormally rapid heart rate, or tachyarrhythmia. When detected, ventricular tachyarrhythmia can be terminated with high-energy shock therapy using an IMD such as an ICD.

Patients that use IMDs may be adversely affected by misinterpretations of signals sensed by the IMD sensing circuits. If an IMD incorrectly interprets a sensed signal as indicating tachyarrhythmia, the IMDs may inappropriately deliver shock therapy. Inappropriate delivery of shock therapy can cause patient discomfort and consumes a relatively large amount of battery power which may lead to a shortened useful device lifetime. Therefore, it is important to accurately detect tachyarrhythmia.

OVERVIEW

This document relates generally to systems, devices, and methods for monitoring cardiac electrophysiological parameters of a patient or subject, and in particular for improved discrimination or classification of heart arrhythmias.

In example 1, an apparatus includes a first implantable sensor that produces a first electrical sensor signal representative of cardiac depolarization events of a heart of a subject, a second implantable sensor that produces a second electrical sensor signal representative of hemodynamic function of the heart, a signal analyzer circuit, and an arrhythmia discrimination circuit. The signal analyzer circuit detects an arrhythmic event from the first sensor signal and calculates hemodynamic stability in response to the arrhythmic event detection using the second sensor signal. The arrhythmia discrimination circuit selects, according to a calculated hemodynamic stability produced by the signal analyzer circuit, an arrhythmia discrimination algorithm from among a plurality of candidate arrhythmia discrimination algorithms that are implementable by the arrhythmia discrimination circuit, classifies the detected arrhythmia using the selected arrhythmia discrimination algorithm, and provides the arrhythmia classification to a user or process.

In example 2, the arrhythmia discrimination circuit of example 1 is optionally configured to select a first arrhythmia discrimination algorithm when the hemodynamic stability calculation indicates that the arrhythmia is hemodynamically stable, and select a second arrhythmia discrimination algorithm when the hemodynamic stability calculation indicates that the arrhythmia is hemodynamically unstable. The first arrhythmia discrimination algorithm has higher specificity than the second arrhythmia discrimination algorithm and the second arrhythmia discrimination algorithm has higher sensitivity than the first arrhythmia discrimination algorithm.

In example 3, the arrhythmia discrimination circuit of any one or more of examples 1 and 2 is optionally configured to quantize a level of hemodynamic stability or instability from a hemodynamic stability calculation, and select an arrhythmia discrimination algorithm according to the level of hemodynamic stability or instability.

In example 4, the apparatus of any one or more of examples 1-3 optionally includes a third sensor configured to produce a third electrical sensor signal representative of physiologic events of the subject. The arrhythmia discrimination circuit is configured to select an arrhythmia discrimination algorithm according to the calculated hemodynamic stability and according to physiologic information obtained from the third sensor signal.

In example 5, the apparatus of any one or more of examples 1-4 optionally includes a storage circuit configured to store information related to at least one of a patient indication or a patient demographic. The arrhythmia discrimination circuit is configured to select an arrhythmia discrimination algorithm according to the calculated hemodynamic stability and according to the at least one of the stored patient indication or patient demographic.

In example 6, the candidate arrhythmia discrimination algorithms of any one or more of examples 1-5 optionally differ from each other in at least one of a feature extracted from the first sensor signal and used by a candidate algorithm in classifying the arrhythmia, a rule used by a candidate algorithm to classify the arrhythmia, or a logic structure of a candidate algorithm.

In example 7, the candidate arrhythmia discrimination algorithms of any one or more of examples 1-6 optionally include a default arrhythmia discrimination algorithm. The arrhythmia discrimination circuit of the examples is configured to determine, according to the calculated hemodynamic stability, whether to use the default algorithm or to switch to a different candidate algorithm.

In example 8, the arrhythmia discrimination circuit of any one or more of examples 1-7 is optionally configured to preselect the plurality of candidate arrhythmia discrimination algorithms from among a set of algorithms implementable by the arrhythmia classification circuit, classify the detected arrhythmia using each of the candidate arrhythmia discrimination algorithms, weight the arrhythmia classifications by the candidate algorithms according to the calculated hemodynamic stability, and ultimately classify the detected arrhythmia according to the weights.

In example 9, the arrhythmia discrimination circuit of any one or more of examples 1-8 is optionally configured to preselect the candidate arrhythmia discrimination algorithms according to at least one of physiologic information obtained from a third electrical sensor signal, a patient indication stored in a memory of the apparatus, or a patient demographic stored in the memory.

In example 10, the signal analyzer circuit of any one or more of examples 1-9 optionally detects the arrhythmic event when detecting a ventricular rate or interval that satisfies an arrhythmia detection rate or interval threshold and that is sustained for a predetermined duration of time or number of beats.

In example 11, a method includes detecting an arrhythmic event of a heart of a subject using an IMD, monitoring an electrical sensor signal that is representative of hemodynamic function of the heart, calculating hemodynamic stability in response to the arrhythmic event detection using the sensor signal, selecting an arrhythmia discrimination algorithm according to the calculated hemodynamic stability from among a plurality of candidate arrhythmia discrimination algorithms that are implementable by the IMD, classifying the detected arrhythmia using the selected arrhythmia discrimination algorithm, and providing the arrhythmia classification to a user or process.

In example 12, the selecting an arrhythmia discrimination algorithm of example 11 optionally includes selecting a first arrhythmia discrimination algorithm when a hemodynamic stability calculation indicates that the arrhythmia is hemodynamically stable, and selecting a second arrhythmia discrimination algorithm when the hemodynamic stability calculation indicates that the arrhythmia is hemodynamically unstable. The first arrhythmia discrimination algorithm has higher specificity than the second arrhythmia discrimination algorithm and the second arrhythmia discrimination algorithm has higher sensitivity than the first arrhythmia discrimination algorithm.

In example 13, the calculating hemodynamic stability of any one or more of examples 11 and 12 optionally includes quantizing a level of hemodynamic stability or instability from a hemodynamic stability calculation, and the selecting an arrhythmia discrimination algorithm includes selecting an algorithm according to the level of hemodynamic stability or instability.

In example 14, the method of any one or more of examples 11-13 optionally includes monitoring a second electrical sensor signal that is representative of physiologic events of the subject, and the selecting an arrhythmia discrimination algorithm includes selecting an arrhythmia discrimination algorithm according to the calculated hemodynamic stability and according to physiologic information obtained from the second sensor signal.

In example 15, the selecting an arrhythmia discrimination algorithm of any one or more of examples 11-14 optionally includes selecting an arrhythmia discrimination algorithm according to the calculated hemodynamic stability and according to at least one of a patient indication or a patient demographic stored in the IMD.

In example 16, the selecting an arrhythmia discrimination algorithm of any one or more of examples 11-15 optionally includes selecting an arrhythmia discrimination algorithm from among candidate algorithms that differ in at least one of a feature extracted from the sensor signal and used by a candidate algorithm to classify a detected arrhythmia, a rule used by a candidate algorithm to classify the arrhythmia, or a logic structure of a candidate algorithm.

In example 17, the candidate algorithms of any one or more of examples 11-16 optionally include a default arrhythmia discrimination algorithm. The selecting an arrhythmia discrimination algorithm optionally includes determining, according to the calculated hemodynamic stability, whether to use the default algorithm or to switch to a more appropriate candidate algorithm.

In example 18, the method of any one or more of examples 11-17 optionally includes preselecting the plurality of candidate arrhythmia discrimination algorithms from among a set of algorithms implementable by the IMD, and classifying the detected arrhythmia using each of the candidate arrhythmia discrimination algorithms. The selecting an arrhythmia discrimination algorithm optionally includes weighting the classifications by the candidate algorithms according to the calculated hemodynamic stability, and the classifying the detected arrhythmia optionally includes using the classification of a candidate arrhythmia discrimination algorithm selected according to the weighting.

In example 19, the preselecting the plurality of candidate algorithms of any one or more of examples 1-18 optionally includes preselecting the candidate arrhythmia discrimination algorithms according to at least one of physiologic information obtained from a second sensor signal, a patient indication stored in the IMD, or a patient demographic stored in the IMD.

In example 20, the detecting the arrhythmic event of any one or more of examples 1-19 optionally includes detecting a ventricular rate or interval that satisfies an arrhythmia detection rate or interval threshold.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for improved detection of cardiac events by an IMD. Specifically systems and methods for improved discrimination or classification of arrhythmias by an IMD are described.

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
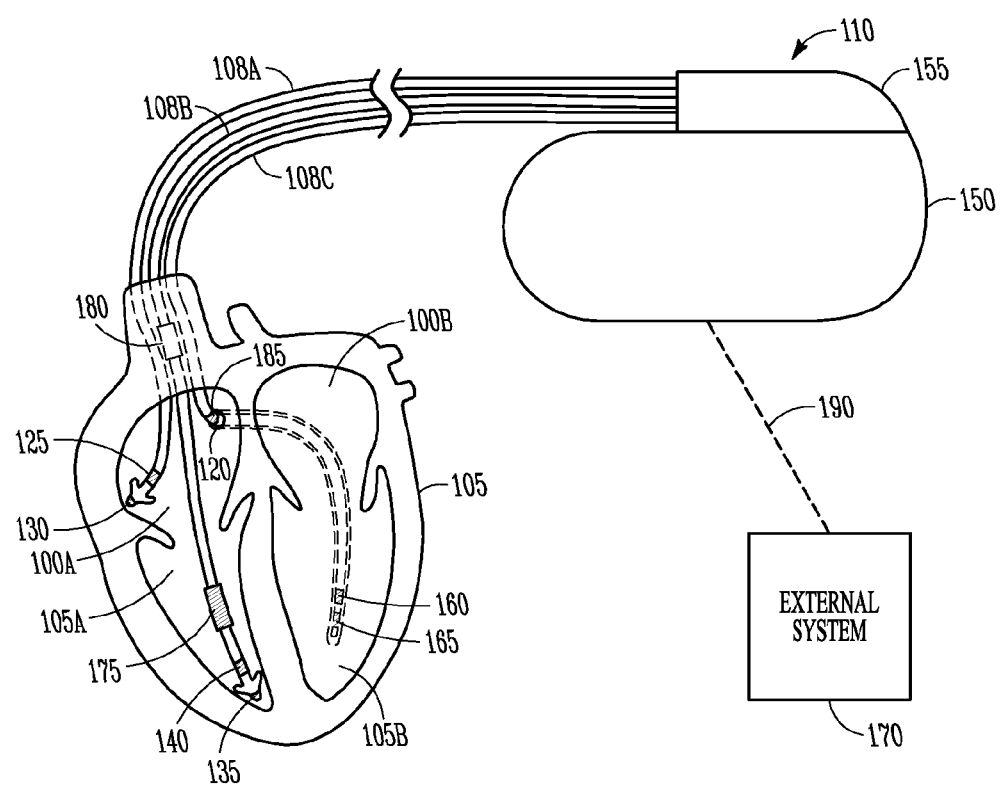
FIG. 1 is an illustration of portions of a system that uses an IMD.

FIG. 1 is an illustration of portions of a system that uses an IMD 110. Examples of IMD 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Atrial lead 108A includes electrodes (electrical contacts, such as ring electrode 125 and tip electrode 130) disposed in an atrium 100A of heart 105 for sensing signals, or delivering pacing therapy, or both, to the atrium 100A.

Ventricular lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105.

The IMD 110 may include a third cardiac lead 108C attached to the IMD 110 through the header 155. The third cardiac lead 108C includes ring electrodes 160 and 165 placed in a coronary vein lying epicardially on the left ventricle (LV) 105B via the coronary vein. The third cardiac lead 108C may include a ring electrode 185 positioned near the coronary sinus (CS) 120.

Lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrical contacts or "electrodes." Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the can 150, or a header 155, would be a second vector.

The efficacy of a medical device in treating abnormally rapid heart rates is often expressed in terms of sensitivity and specificity. Sensitivity generally refers to the ability of the detection scheme of a device to effectively detect an abnormal heart rhythm that the device is to treat (e.g., ventricular tachycardia (VT) or ventricular fibrillation (VF), and/or to discriminate between different abnormal rhythms or noise). The sensitivity can be expressed as follows:

$$\text{Sensitivity} = \text{True Positives}/(\text{True Positives} + \text{False Negatives}).$$

Specificity refers to the ability of the detection scheme of a device to avoid treating those rhythms that the device is not intended to treat (e.g., Sinus Tachycardia (ST)). The specificity can be expressed as follows:

$$\text{Specificity} = \text{True Negatives}/(\text{True Negatives} + \text{False Positives}).$$

For example, if the rhythm to be detected is a tachyarrhythmia such as VT/VF, then a true positive would occur when a particular rhythm is VT/VF and the detection algorithm correctly discriminates it as VT/VF. A false negative would occur when the rhythm is VT/VF and the detection algorithm erroneously declares it as not an arrhythmia or discriminates it as an arrhythmia different from VT/VF. A false positive would occur when the rhythm is anything but VT/VF (e.g., normal sinus rhythm (NSR), ST, atrial fibrillation (AF), atrial flutter (AFl), electrical noise (e.g., due to mypotentials, electromagnetic interference (EMI), a loose set screw for a leadwire, a broken leadwire, etc.)) and the discrimination algorithm erroneously declares it as VT/VF. A true negative would occur when the rhythm is anything but VT/VF (e.g., NSR, ST, AF, AFl, electrical noise, etc.) and the discrimination algorithm correctly declares it as not VT/VF.

In practice, designing an arrhythmia discrimination scheme for a medical device involves settling for a trade-off between sensitivity and specificity. This is because of the technical difficulty in creating a discrimination algorithm that works universally for all patients regardless of their heart condition. Detection and discrimination schemes are generally conservatively designed to err on the side of increasing sensitivity at the expense of specificity. This is to ensure that the benefit of such schemes (i.e., properly treating life threatening arrhythmias) outweighs the cost of the schemes (i.e., inappropriately delivering therapy, especially painful shock therapy).

In comparison to trying to develop a universal arrhythmia detection and discrimination algorithm, it is relatively easier to develop an algorithm that has a high degree of sensitivity but low to moderate specificity, or to develop an algorithm that has a high degree of specificity but low to moderate sensitivity.

Rather than try to implement one arrhythmia discrimination algorithm in an IMD and try to find the best fit for that algorithm for a patient, a better approach to achieve the best arrhythmia discrimination is to implement several tachyarrhythmia discrimination algorithms in an IMD and provide a way for the IMD to automatically select among the different algorithms for the patient's current situation. Hemodynamic information that is sensed or measured by the device is useful in determining which algorithm to use.

Figure 2:
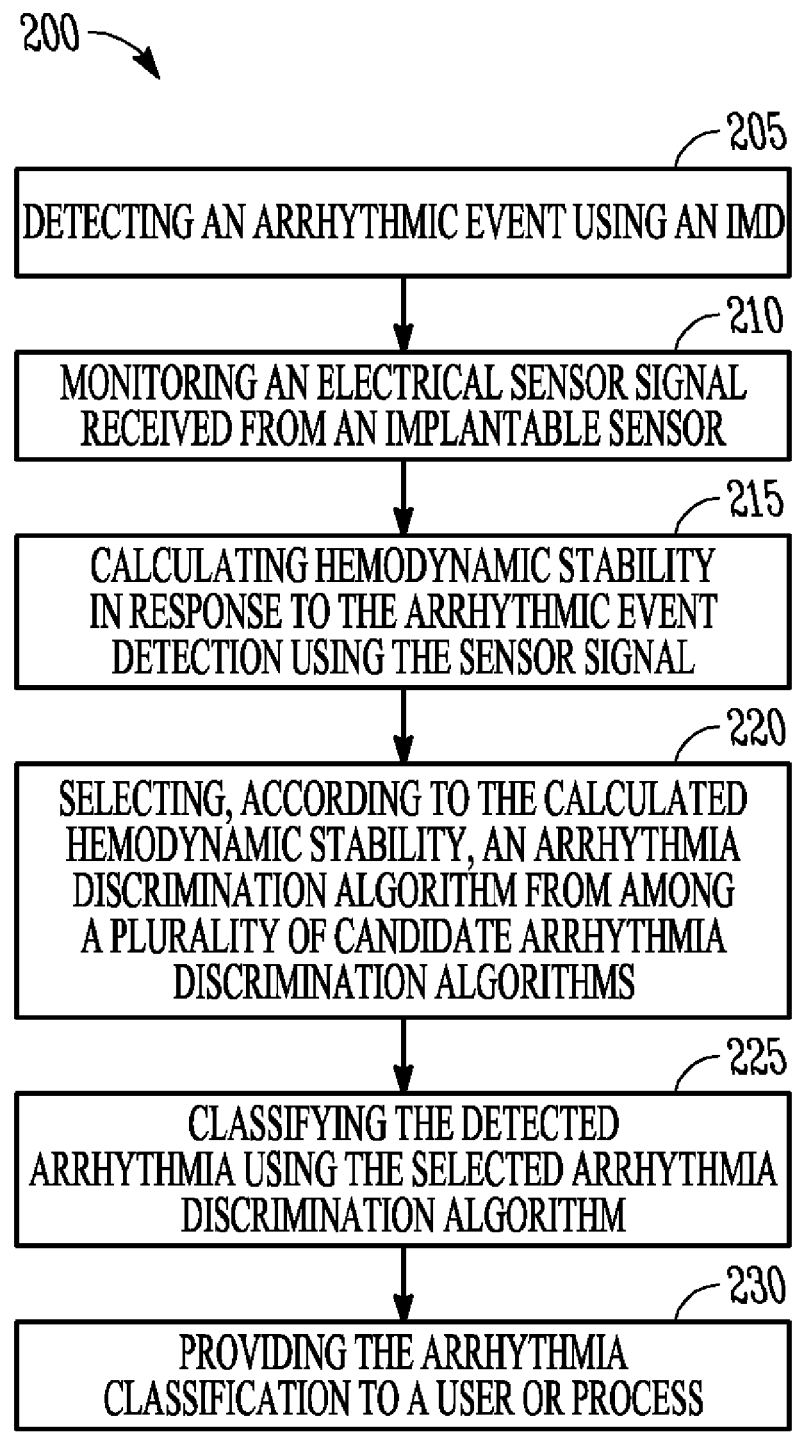
FIG. 2 is a flow diagram of a method of implementing arrhythmia discrimination in an IMD.

FIG. 2 is a flow diagram of a method 200 of implementing arrhythmia discrimination in an IMD. At block 205, an arrhythmic event of a heart of a subject is detected using the IMD. In some examples, the arrhythmia is a tachyarrhythmia such as, among other things, VT, VF, supraventricular tachycardia (SVT), ST, AF, or AFl. In certain examples, the IMD senses cardiac depolarization signals and detects tachyarrhythmia by detecting a depolarization rate that exceeds a tachyarrhythmia detection rate threshold.

At block 210, an electrical sensor signal received from an implantable sensor is monitored. The electrical sensor signal is representative of hemodynamic function of the heart. Hemodynamic function refers to the efficacy of the mechanical function of the heart (e.g., the contractility of the heart). It should be noted this is different from sensing electrical intrinsic cardiac signals which are the action potentials that propagate through the heart's electrical conduction system.

In some examples, the electrical sensor signal is indicative of cardiac output during the arrhythmic event. This may include an electrical signal provided by an implantable cardiac blood pressure sensor. A description of systems and methods that use an implantable pressure sensor is found in Salo et al., U.S. Pat. No. 6,666,826, entitled "Method and Apparatus for Measuring Left Ventricular Pressure," filed Jan. 4, 2002, which is incorporated herein by reference in its entirety. Other cardiac pressure sensors examples include a right ventricle (RV) chamber pressure sensor, a pulmonary artery pressure sensor, and a left atrial chamber pressure sensor. Another sensor that provides an electrical sensor signal indicative of cardiac output is a blood flow sensor.

In some examples, the electrical sensor signal is indirectly indicative of cardiac output during the arrhythmic event. Examples of sensors that provide an electrical signal indirectly indicative of hemodynamic function include, among other things, an intracardiac impedance sensor, a transthoracic impedance sensor, a heart sound sensor, a temperature sensor, and a chemical sensor.

Electrodes placed within a chamber of the heart provide a signal of intracardiac impedance versus time. The electrodes may be placed in a right ventricle of the heart and the measured intracardiac impedance waveform can be signal processed to obtain a measure of the time interval beginning with a paced or spontaneous QRS complex (systole marker) and ending with a point where the impedance signal crosses the zero axis in the positive direction following the QRS complex. The resulting time interval is inversely proportional to the contractility of the heart. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety. Examples of a transthoracic impedance sensor is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety.

Monitoring heart sounds allows a physician to observe or assess the hemodynamic performance of a patient. A change in heart chamber contractility can be measured using a heart sound sensor. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference in its entirety.

An implantable cardiac temperature sensor can provide information indirectly indicative of cardiac output. In some examples, an implantable cardiac temperature sensor is included in a lead system implanted into the coronary sinus of a patient. The implantable cardiac temperature sensor measures the temperature of the blood returning through the coronary sinus after having passed through myocardial tissue. As a byproduct of normal cardiac function, the heart generates heat. This heat is extracted by the perfusing blood. The blood exits through the coronary veins into the coronary sinus before passing into the right atrium and right ventricle. The blood is then pumped through the lungs where the excess heat is removed and passed out of the body with the exhaled air.

The useful work ($W_u$) performed by the left ventricle relates to the volume of blood moved through the ventricle, whereas the heat output from the left ventricle is related to total work ($W_T$). The difference in temperature between blood entering the left ventricle and blood in a coronary vein is related to left ventricular work. An increase in $W_T$, or cardiac temperature as a surrogate measurement, that is not accompanied by other indications of increased activity or patient exertion, may indicate a lowering of efficiency of a patient's hemodynamic system.

An approach to sensing temperature within a coronary vein is found in Salo, Patent Application Publ. No. 2003/0125774, entitled "Method and Apparatus for Monitoring Left Ventricular Work or Power," filed Dec. 31, 2001, which is incorporated herein by reference in its entirety.

An example of a chemical sensor that can provide information indirectly indicative of cardiac output is an implantable oxygen saturation sensor. An oxygen saturation sensor produces an electrical sensor signal related to changes in the fluid oxygen saturation associated with the heart's mechanical activity, contractility, and blood flow. A change in contractility may be manifested as reduced levels in blood oxygen saturation levels. An approach for using an implantable sensor to measure blood oxygen saturation levels is found in Thompson, U.S. Pat. No. 5,342,406, entitled "Oxygen Sensor Based Capture Detection for a Pacer," filed Oct. 7, 1992, which is incorporated herein by reference in its entirety.

Regarding the method in FIG. 2, the electrical sensor signal received from the implantable sensor is used to characterize the degree of hemodynamic stability or instability. At block 215, hemodynamic stability is calculated in response to the arrhythmic event detection using the sensor signal. Features are extracted from the electrical sensor signal. Values of the features are quantized to discrete levels. Changes in the levels reflect changes in the hemodynamic stability of the subject as a result of arrhythmia.

Figure 3:
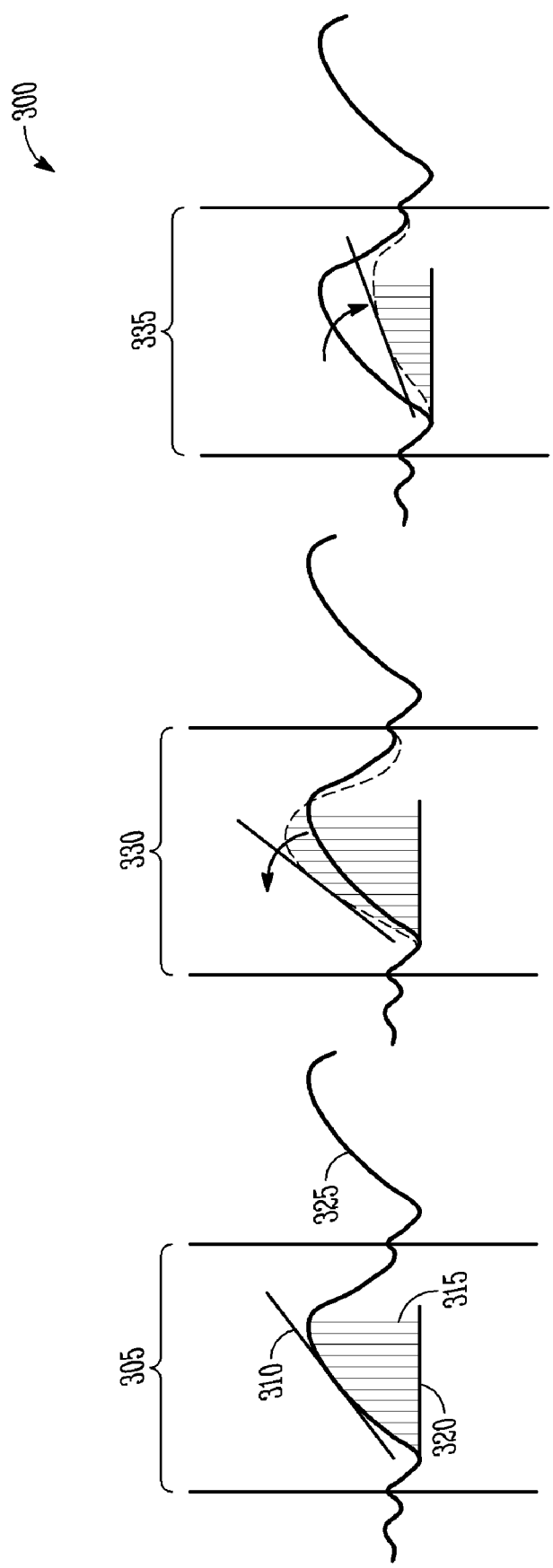
FIG. 3 shows a set of graphs of measured intracardiac impedance waveforms.

An example is shown in FIG. 3. FIG. 3 shows a set of graphs 300 of measured intracardiac impedance waveforms. Graph 305 illustrates a slope 310 of the waveform and an area 315 above a baseline intracardiac impedance value 320 and below an intracardiac impedance waveform 325. The slope 310 and/or the area 315 are extracted from the impedance waveform 325. Graph 330 illustrates a change in intracardiac impedance that increases the slope of the waveform and the area under the waveform and above the baseline value. Because intracardiac impedance is inversely proportional to volume, the change may indicate an increase in the change in volume of blood filling the ventricles and being emptied from the ventricles during a cardiac cycle. Graph 335 illustrates a change that decreases the slope and the area, and thus may indicate that the volume of blood flow is not changing to the same degree as in graph 305 and graph 330, possibly because the ventricles are not emptying properly. If the slope or the area rapidly decreases over cardiac cycles, this may be an indication of hemodynamic instability.

Examples of assessing hemodynamic performance using intracardiac impedance are found in Zhang et al., U.S. Patent Pub. No. 2007/0043394, "Intracardiac Impedance and its Applications," filed Aug. 22, 2005, which is incorporated herein by reference in its entirety.

Returning to FIG. 2, at block 220, an arrhythmia discrimination algorithm is selected according to the calculated hemodynamic stability. The arrhythmia discrimination algorithm is selected from among a plurality of candidate arrhythmia discrimination algorithms that are implementable by the IMD.

At block 225, the detected arrhythmia is classified using the selected arrhythmia discrimination algorithm. At block 230, the arrhythmia classification is provided to a user or process.

Figure 4:
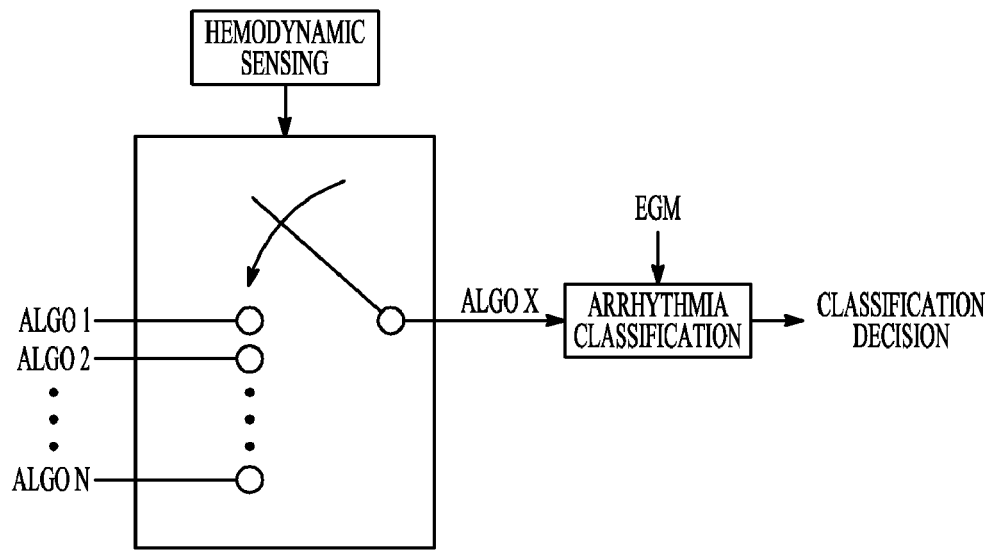
FIG. 4 is a conceptual block diagram of an example of an arrhythmia discrimination algorithm.

Conceptually, an example of this discrimination algorithm selection is shown in FIG. 4. An arrhythmic event of a heart of a subject is detected using a cardiac signal sensing circuit such as an electrogram (EGM) circuit. An arrhythmia discrimination algorithm (Algorithm X) is selected from among N candidate algorithms according to an assessment of hemodynamic stability determined from the hemodynamic sensing. The selected algorithm then uses information provided by the cardiac signal sensing circuit to classify the arrhythmia.

Figure 5:
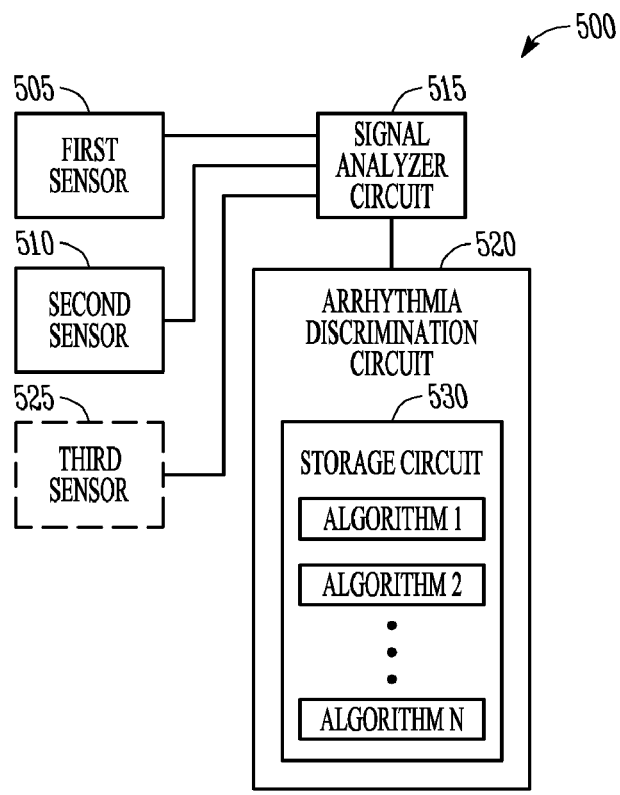
FIG. 5 is a block diagram of portions of an IMD to detect and discriminate among arrhythmias.

FIG. 5 is a block diagram of portions of an IMD 500 to detect and discriminate among arrhythmias. The IMD 500 includes a first implantable sensor 505 and a second implantable sensor 510. In some examples, the first implantable sensor 505 includes a cardiac signal sensing circuit and produces a first electrical sensor signal representative of cardiac depolarization events of a heart of a subject.

The IMD 500 also includes a signal analyzer circuit 515 communicatively coupled to the first and second implantable sensors. The communicative coupling allows the signal analyzer circuit 515 to receive electrical signals from the first and second implantable sensors even though there may be intervening circuitry between them.

In some examples, the signal analyzer circuit 515 detects an arrhythmia using the first sensor signal by detecting a depolarization rate that exceeds an arrhythmia detection rate threshold. For example, the signal analyzer circuit 515 may detect a ventricular depolarization rate or interval that satisfies an arrhythmia detection rate or interval threshold. In certain examples, the signal analyzer circuit 515 detects tachyarrhythmia when the rate or interval is sustained for a predetermined duration of time or number of beats.

In some examples, the signal analyzer circuit 515 detects arrhythmia using an assessment of heart rhythm stability when a subject experiences a sudden increase in heart rate. Examples of methods and systems to detect arrhythmia and assess the stability of the rhythms are found in Gilkerson et al., U.S. Pat. No. 6,493,579, entitled "System and Method for Detection Enhancement Programming," filed Aug. 20, 1999, which is incorporated herein by reference in its entirety.

The second implantable sensor 510 produces a second electrical sensor signal representative of hemodynamic function of the heart. As described previously, a non-exhaustive list of examples of the second implantable sensor 510 includes an implantable cardiac blood pressure sensor, an implantable blood flow sensor, an intracardiac impedance sensor, a transthoracic impedance sensor, a heart sound sensor, a temperature sensor, and a chemical sensor. Further examples includes sensors to monitor heart valve motion and ventricular wall motion. In response to the detection of an arrhythmic event, the signal analyzer circuit 515 calculates hemodynamic stability using the second sensor signal.

The IMD 500 includes an arrhythmia discrimination circuit 520 communicatively coupled to the signal analyzer circuit 515 and at least the first implantable sensor 505. The arrhythmia discrimination circuit 520 is able to implement two or more different discrimination algorithms. In some examples, the arrhythmia discrimination circuit 520 includes a processor and the algorithms are embodied in instructions in software or firmware that are performable by the processor. Such a processor may include a microprocessor or application specific integrated circuit (ASIC). In some examples, the signal analyzer circuit 515 and the arrhythmia discrimination circuit 520 are included in the same processor, such as a digital signal processor (DSP).

The discrimination algorithms differ in the way they identify or discriminate among arrhythmias. The algorithms differ in at least one of the following: in the features extracted from the sensor signals that they use, in rules they use for detection, and in the structure of their decision-making logic.

For instance, to classify a type of tachyarrhythmia, one discrimination algorithm may use a depolarization rate extracted from the sensor signals to classify the arrhythmia. Another algorithm may use rate onset extracted from the sensor signals. In rate onset a current depolarization rate is compared to a running average of the rate. If the current rate changes (e.g., increases) by more than a threshold value from the running average within a number of cardiac cycles, sudden onset is declared. Another algorithm may use gradual onset, where the rate is gradually changing from the running average within a certain percentage each cardiac cycle. Another feature is ventricular to ventricular (V-V) interval stability. In addition to detection using heart stability as described previously, an algorithm may use V-V stability to classify the arrhythmia.

Still another algorithm may use morphology similarity to a template to classify the arrhythmia. An arrhythmia may be classified by comparing the morphology of first sensor signal to a morphology template stored in a memory of the arrhythmia discrimination circuit 520. In some examples, the morphology of a sensed cardiac depolarization is compared to a template of a known normal or abnormal depolarization morphology (such as normal sinus rhythm, ventricular tachyarrhythmia, or supra-ventricular tachyarrhythmia) stored in the memory. For example, a template can be created for a patient using a CRM by providing electrical energy pulses to the supra-ventricular region of the patient's heart. The resulting cardiac complexes are then sensed and used to create a template for use in a morphology-based cardiac signal classification algorithm. Systems and methods of creating templates for a morphology-based algorithm are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference in its entirety.

In another example, an algorithm may use beat morphology stability to classify an arrhythmia. In some examples of beat morphology analysis, a plurality of feature correlation coefficient (Fcc) values each associated with an arrhythmic heart beat of a plurality of heart beats is sensed during a detected arrhythmia. Each Fcc value indicates whether the associated arrhythmic heart beat is morphologically correlated to a template heart beat of a known type cardiac rhythm. Majority voting is used to classify the arrhythmia as a particular type of arrhythmia (e.g., a particular type of tachyarrhythmia). That is, if the number of the arrhythmic heart beats that are correlated to the template heart beat equals or exceeds a predetermined threshold number, the arrhythmia is classified as that particular type arrhythmia represented by the template.

If the number of the arrhythmic heart beats that are correlated to the template heart beat is smaller than the predetermined threshold number, the stability of the morphology as indicated by the Fcc values is analyzed to further classify the arrhythmia based the stability of morphology. In some examples, the variance of the Fcc values produced by the correlation analysis for the analyzed arrhythmic heart beats is analyzed to discriminate the arrhythmia. Systems and methods to discriminate arrhythmia using morphology stability may be found in Li, U.S. Pat. No. 7,430,446, "Methods and Apparatuses for Cardiac Arrhythmia Classification Using Morphology Stability, filed Jan. 20, 2005, which is incorporated herein in its entirety.

As stated above, the discrimination algorithms implementable by the arrhythmia discrimination circuit 520 may differ in the rules they use for detection. For example, one algorithm may use sudden onset to discriminate the arrhythmia while another algorithm may use gradual onset. In certain examples, two algorithms may differ in the rule applied to detect gradual onset or sudden onset. For instance, one algorithm may declare sinus tachycardia when detecting a gradual onset where the depolarization rate is gradually changing from a running average by less than 9% each cardiac cycle. Another algorithm may use a different rule (e.g., a different percentage) for gradual onset to declare sinus tachycardia.

In some examples, the discrimination algorithms differ in their decision-making logic. For instance, one discrimination algorithm may use a decision tree, a second discrimination algorithm may use majority voting, a third discrimination algorithm may use fuzzy logic, and a fourth algorithm may implement a neural net.

In certain examples, the discrimination algorithms differ in the structure of their decision-making logic. For instance, assume two algorithms each use a decision tree to discriminate among detected arrhythmias and that the decision trees are composed of a set or series of IF-THEN statements. In this example, the first algorithm is a rhythm identification algorithm (Rhythm ID) and the second algorithm is a detection enhancement algorithm. The two algorithms may differ in the IF-THEN statements used for the discrimination. The Rhythm ID algorithm may first check if a rate threshold is exceeded. If so, then the Rhythm ID algorithm then checks if the ventricular rate exceeds the atrial rate (V>A). The Rhythm ID algorithm then checks for rate onset, determines rate stability, and checks for atrial fibrillation, in this order.

The detection enhancement algorithm may have its IF-THEN statements arranged in the following different order: first a check if a rate threshold is exceeded, then a check if V>A, followed by a morphology analysis of vector timing and correlation (VTC), then a check for atrial fibrillation followed by a determination of rate stability.

As stated above in regard to FIG. 5, the arrhythmia discrimination circuit 520 is able to implement two or more different discrimination algorithms. The arrhythmia discrimination circuit 520 selects a discrimination algorithm to use in discriminating the detected arrhythmia from among a plurality of different candidate arrhythmia discrimination algorithms that are implementable by the arrhythmia discrimination circuit 520. The discrimination algorithm is selected according to the calculated hemodynamic stability produced by the signal analyzer circuit 515.

If the hemodynamic stability calculation indicates that the subject is hemodynamically stable, then the arrhythmia is tolerable by the subject. The subject is relatively safe during the arrhythmia, and a discrimination algorithm with high specificity may be used by the IMD 500. Conversely, if the calculation indicates that the subject is hemodynamically unstable, then the arrhythmia is not likely to be tolerable by the subject. The arrhythmia may be life threatening, and a discrimination algorithm with high sensitivity may be more appropriate to ensure that proper therapy for the arrhythmia is delivered. For example, if the second sensor 510 is an implantable cardiac blood pressure sensor, the signal analyzer circuit may determine to use a discrimination algorithm having high sensitivity if the signal analyzer circuit 515 determines that the blood pressure of the subject has dropped below a specified threshold.

Therefore, in some examples the arrhythmia discrimination circuit 420 is configured to select a first arrhythmia discrimination algorithm when the hemodynamic stability calculation indicates that the arrhythmia is hemodynamically stable, and select a second arrhythmia discrimination algorithm when the hemodynamic stability calculation indicates that the arrhythmia is hemodynamically unstable. The first arrhythmia discrimination algorithm has higher specificity than the second arrhythmia discrimination algorithm and the second arrhythmia discrimination algorithm has higher sensitivity than the first arrhythmia discrimination algorithm.

Figure 6:
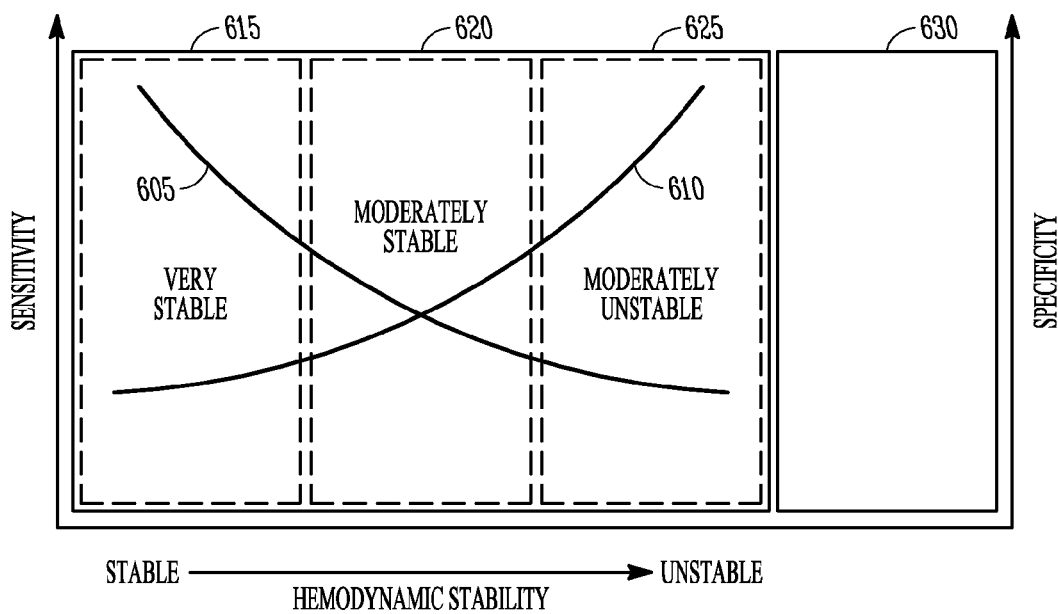
FIG. 6 shows graphs of hemodynamic stability with algorithm sensitivity and specificity.

FIG. 6 shows graphs 605, 610 of hemodynamic stability with algorithm sensitivity and specificity. In some examples, the arrhythmia discrimination circuit 520 quantizes the level of hemodynamic stability or instability from the hemodynamic stability calculation. The arrhythmia discrimination circuit 520 selects an arrhythmia discrimination algorithm according to the level of hemodynamic stability or instability. Graph 605 indicates an example of a lower bound of the specificity requirement for a discrimination algorithm as the quantized level of hemodynamic stability varies. Graph 610 indicates an example of a lower bound of the sensitivity requirement for the discrimination algorithm.

In the example, hemodynamic stability is divided into four stability zones 615, 620, 625, and 630. In zone 615, the subject is hemodynamically very stable, so a discrimination algorithm with high specificity is chosen by the arrhythmia discrimination circuit 520 to classify the arrhythmia. In zone 620, the subject is moderately hemodynamically stable, so a discrimination algorithm with high sensitivity is chosen by the arrhythmia discrimination circuit 520 to classify the arrhythmia. In zone 625, the subject is moderately hemodynamically stable. In this zone, the choice of whether to use high specificity or sensitivity is less clear. In certain examples, the logic used in implementing the selection may be weighted to select those discrimination algorithms that relatively more successful in discriminating arrhythmia for that subject. In zone 630, the subject is very hemodynamically unstable. In some examples, the selecting of a discrimination algorithm by the arrhythmia discrimination circuit 520 is disabled or bypassed and a default highly sensitive algorithm is used. In certain examples, the zone boundaries are programmable by a physician.

The arrhythmia discrimination circuit 520 then classifies the detected arrhythmia using the selected arrhythmia discrimination algorithm. When the classification of an arrhythmia is complete, the arrhythmia discrimination circuit 520 may provide the arrhythmia classification to a user or process. In some examples, the classification may be used by the IMD 500 to begin an anti-tachyarrhythmia treatment such as anti-tachycardia pacing (ATP) or delivery of an anti-tachyarrhythmia drug. In some examples, the classification is communicated to an external device, such as an IMD programmer or advanced patient management (APM) system. Accurate classification of arrhythmia such as tachyarrhythmia reduces inappropriate delivery of shock therapy, and may help ensure proper device function. In another example, accurate classification of arrhythmia such as AF allows the IMD to correctly perform a mode switch function (e.g., from a DDD pacing mode to a VVI pacing mode) when AF is present.

In some examples, the IMD 500 includes a third sensor 525 that produces a third electrical sensor signal representative of physiologic events of the subject. The arrhythmia discrimination circuit 520 selects an arrhythmia discrimination algorithm according to the calculated hemodynamic stability and according to physiologic information obtained from the third sensor signal. This additional physiological information can be used to assess the tolerability of the arrhythmia. For instance, in certain examples the third sensor 525 includes a posture sensor. If the posture sensor indicates that the subject remains standing during the arrhythmia, rather than sitting or lying down, this may indicate that the arrhythmia is tolerable to the subject and an algorithm with higher specificity can be used to classify the arrhythmia.

In some examples, the IMD 500 includes a storage circuit 530 (e.g., a memory) communicatively coupled to the arrhythmia discrimination circuit. The storage circuit 530 may be integral to or separate from the arrhythmia discrimination circuit 520. The storage circuit 530 stores information related to at least one of a patient indication (e.g., a type of heart disease of the subject, whether the subject has experienced heart failure, etc.) or a patient demographic (e.g., subject's age, subject's gender, etc.). The arrhythmia discrimination circuit 520 selects an arrhythmia discrimination algorithm according to the calculated hemodynamic stability and according to the stored patient indication or patient demographic.

For example, if the storage circuit 530 includes an indication that the subject has experienced heart failure (HF), then the arrhythmia discrimination circuit 520 may be configured (e.g., programmed) to be conservative and select a discrimination algorithm with higher specificity than for a subject without HF.

In some examples, the candidate algorithms include a default arrhythmia discrimination algorithm. The arrhythmia discrimination circuit 520 determines, according to the calculated hemodynamic stability, whether to use the default algorithm or to switch to a different candidate algorithm. For instance, a physician may preselect a default algorithm with high specificity for subjects with a high degree of atrial-ventricular (AV) block, or with an atrial-ventricular node ablation (AVN), or with an NYHA classification of III. The arrhythmia discrimination circuit 420 determines, using information provided by the hemodynamic and/or physiologic sensors, whether to use a discrimination algorithm of lower sensitivity and higher specificity.

Figure 7:
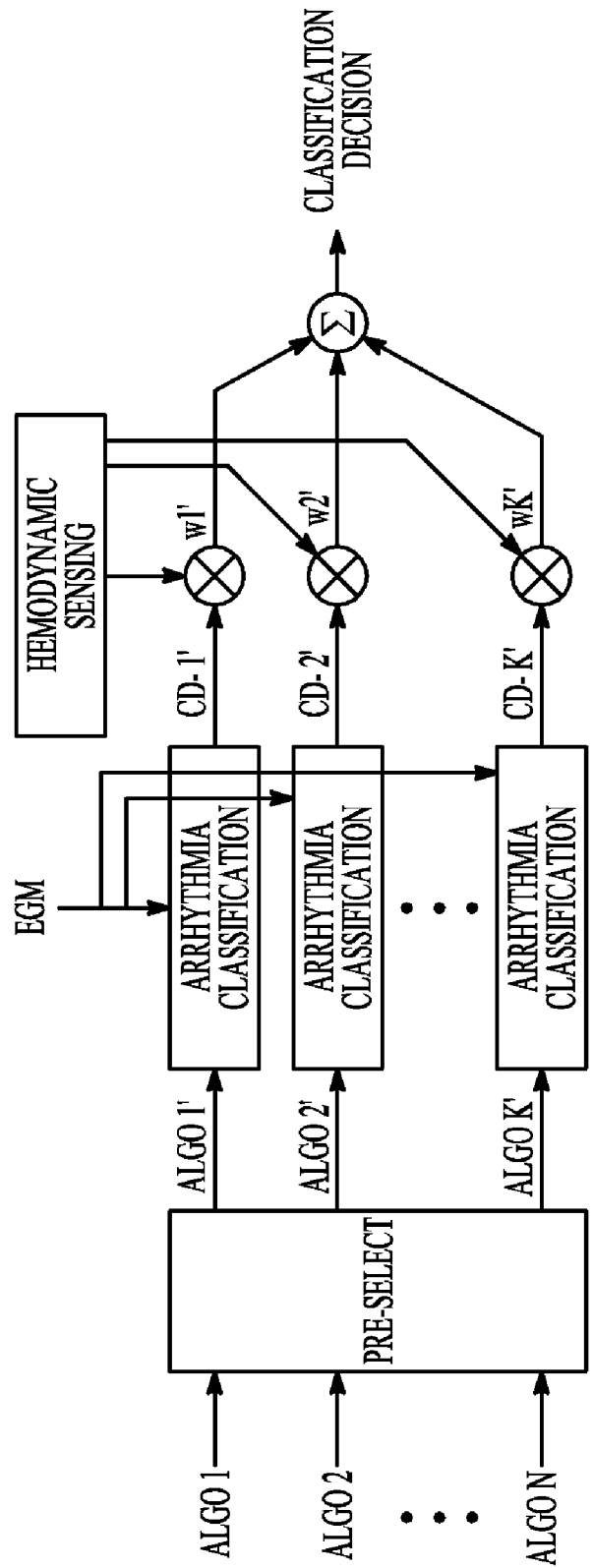
FIG. 7 is a conceptual block diagram of an example of another arrhythmia discrimination algorithm.

According to some examples, the arrhythmia discrimination circuit 520 preselects a plurality of k candidate arrhythmia discrimination algorithms out of the N algorithms implementable by the arrhythmia discrimination circuit 520. This is shown conceptually in the block diagram of FIG. 7. In some examples, the k preselected algorithms are chosen by the arrhythmia discrimination circuit 520 using the previously described patient indications and/or patient demographics stored in a memory of the IMD 500, using physiologic information obtained from a third electrical sensor signal, or chosen by a physician as k default algorithms.

The detected arrhythmia is classified by each of the k preselected candidate arrhythmia discrimination algorithms using the first sensor signal (e.g., an electrogram provided by a cardiac signal sensing circuit), resulting in k classification decisions. The hemodynamic sensing and calculation of hemodynamic stability provided by the signal analyzer circuit 515 and a signal provided by a third physiologic sensor (if any) is used to control the output of a decision fusion rule that determines the final classification decision.

In some examples, the decision fusion rule includes a weighted sum of the classification decisions provided by each of the k preselected arrhythmia discrimination algorithms. The arrhythmia classifications by the k candidate algorithms are weighted according to the calculated hemodynamic stability. In certain examples, the weights are assigned based on the output of the hemodynamic sensor or the physiologic sensor. If the calculation of hemodynamic stability indicates that the subject is hemodynamically stable during the arrhythmia, then a higher weight is assigned to one of the k algorithms that has a higher specificity. If the calculation of hemodynamic stability indicates that the subject is hemodynamically unstable during the arrhythmia, then a higher weight is to one of the k algorithms that has a higher sensitivity.

The detected arrhythmia is ultimately classified according to the weights. In some ways, the single algorithm approach of FIG. 4 is a special case of this multiple algorithm preselection approach. This can be seen if the weight assigned to each non-selected algorithm of the k algorithms is assigned a weight of zero.

Additional Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    a first implantable sensor configured to produce a first electrical sensor signal representative of cardiac depolarization events of a heart of a subject;
    a second implantable sensor configured to produce a second electrical sensor signal representative of hemodynamic function of the heart;
    a signal analyzer circuit, communicatively coupled to the first and second implantable sensors, configured to:
        detect an arrhythmic event from the first sensor signal; and
        calculate hemodynamic stability in response to the arrhythmic event detection using the second sensor signal; and
    an arrhythmia discrimination circuit, communicatively coupled to the signal analyzer circuit and the first implantable sensor, configured to:
        preselect the plurality of candidate arrhythmia discrimination algorithms from among a set of algorithms implementable by the arrhythmia classification circuit;
        classify the detected arrhythmia using each of the candidate arrhythmia discrimination algorithms;
        weight the arrhythmia classifications by the candidate algorithms according to the calculated hemodynamic stability;
        ultimately classify the detected arrhythmia according to the weights; and
        provide the arrhythmia classification to a user or process.

2. The apparatus of claim 1, wherein the arrhythmia discrimination circuit is configured to:
    weight a first arrhythmia discrimination algorithm greater than a second arrhythmia discrimination algorithm when the hemodynamic stability calculation indicates that the arrhythmia is hemodynamically stable; and
    weight the second arrhythmia discrimination algorithm greater than the first arrhythmia discrimination algorithm when the hemodynamic stability calculation indicates that the arrhythmia is hemodynamically unstable, wherein the first arrhythmia discrimination algorithm has higher specificity than the second arrhythmia discrimination algorithm and the second arrhythmia discrimination algorithm has higher sensitivity than the first arrhythmia discrimination algorithm.

3. The apparatus of claim 1, wherein the arrhythmia discrimination circuit is configured to:
    quantize a level of hemodynamic stability or instability from a hemodynamic stability calculation; and
    weight an arrhythmia discrimination algorithm according to the level of hemodynamic stability or instability.

4. The apparatus of claim 1, including a third sensor configured to produce a third electrical sensor signal representative of physiologic events of the subject, and wherein the arrhythmia discrimination circuit is configured to select an arrhythmia discrimination algorithm according to the calculated hemodynamic stability and according to physiologic information obtained from the third sensor signal.

5. The apparatus of claim 1, including:
    a storage circuit, communicatively coupled to the arrhythmia discrimination circuit, configured to store information related to at least one of a patient indication or a patient demographic, and
    wherein the arrhythmia discrimination circuit is configured to select an arrhythmia discrimination algorithm according to the weighting using the calculated hemodynamic stability and according to the at least one of the stored patient indication or patient demographic.

6. The apparatus of claim 1, wherein the candidate algorithms differ from each other in at least one of:
    a feature extracted from the first sensor signal and used by a candidate algorithm in classifying the arrhythmia;
    a rule used by a candidate algorithm to classify the arrhythmia; or
    a logic structure of a candidate algorithm.

7. The apparatus of claim 1, wherein the candidate algorithms include a default arrhythmia discrimination algorithm, and wherein the arrhythmia discrimination circuit is configured to determine, according to the calculated hemodynamic stability, whether to use the default algorithm or to switch to a different candidate algorithm.

8. The apparatus of claim 1, wherein the arrhythmia discrimination circuit is configured to preselect the candidate arrhythmia discrimination algorithms according to at least one of:
    physiologic information obtained from a third electrical sensor signal;
    a patient indication stored in a memory of the apparatus; or
    a patient demographic stored in the memory.

9. The apparatus of claim 1, wherein the signal analyzer circuit detects the arrhythmic event when detecting a ventricular rate or interval that satisfies an arrhythmia detection rate or interval threshold and that is sustained for a predetermined duration of time or number of beats.

10. A method comprising:
    detecting an arrhythmic event of a heart of a subject using an implantable medical device (IMD);
    monitoring an electrical sensor signal received from an implantable sensor, wherein the electrical sensor signal is representative of hemodynamic function of the heart;
    calculating hemodynamic stability in response to the arrhythmic event detection using the sensor signal;
    preselecting a plurality of candidate arrhythmia discrimination algorithms from among a set of algorithms implementable by the IMD;

classifying the detected arrhythmia using each of the candidate arrhythmia discrimination algorithms;

weighting the classifications by the candidate algorithms according to the calculated hemodynamic stability;

selecting the arrhythmia classification of a candidate arrhythmia discrimination algorithm according to the weighting; and providing the arrhythmia classification to a user or process.

11. The method of claim 10, wherein weighting an arrhythmia discrimination algorithm includes:

weighting a first arrhythmia discrimination algorithm greater than a second arrhythmia discrimination algorithm when a hemodynamic stability calculation indicates that the arrhythmia is hemodynamically stable; and weighting the second arrhythmia discrimination algorithm greater than the first arrhythmia discrimination algorithm when the hemodynamic stability calculation indicates that the arrhythmia is hemodynamically unstable, wherein the first arrhythmia discrimination algorithm has higher specificity than the second arrhythmia discrimination algorithm and the second arrhythmia discrimination algorithm has higher sensitivity than the first arrhythmia discrimination algorithm.

12. The method of claim 10, wherein calculating hemodynamic stability includes quantizing a level of hemodynamic stability or instability from a hemodynamic stability calculation, and wherein weighting an arrhythmia discrimination algorithm includes weighting an algorithm according to the level of hemodynamic stability or instability.

13. The method of claim 10, including monitoring a second electrical sensor signal, wherein the second sensor signal is representative of physiologic events of the subject, and wherein selecting an arrhythmia discrimination algorithm includes selecting an arrhythmia discrimination algorithm according to the calculated hemodynamic stability and according to physiologic information obtained from the second sensor signal.

14. The method of claim 10, wherein selecting an arrhythmia discrimination algorithm includes selecting an arrhythmia discrimination algorithm according to the weighting using the calculated hemodynamic stability and according to at least one of a patient indication or a patient demographic stored in the IMD.

15. The method of claim 10, wherein preselecting an arrhythmia discrimination algorithm includes preselecting an arrhythmia discrimination algorithm from among candidate algorithms that differ in at least one of:

a feature extracted from the sensor signal and used by a candidate algorithm to classify a detected arrhythmia;

a rule used by a candidate algorithm to classify the arrhythmia; or a logic structure of a candidate algorithm.

16. The method of claim 10, wherein the candidate algorithms include a default arrhythmia discrimination algorithm, and wherein selecting an arrhythmia discrimination algorithm includes determining, according to the calculated hemodynamic stability, whether to use the default algorithm or to switch to a more appropriate candidate algorithm.

17. The method of claim 10, wherein preselecting the plurality of candidate algorithms includes preselecting the candidate arrhythmia discrimination algorithms according to at least one of:

physiologic information obtained from a second sensor signal;

a patient indication stored in the IMD; or a patient demographic stored in the IMD.

18. The method of claim 10, wherein detecting an arrhythmic event includes detecting a ventricular rate or interval that satisfies an arrhythmia detection rate or interval threshold.

* * * * *